United States Patent [19]
Swenson et al.

[11] Patent Number: 6,113,922
[45] Date of Patent: Sep. 5, 2000

[54] COMPOSITIONS EXPRESSING A PRESSURE OF CARBON DIOXIDE FOR IMPROVED HEALING OF WOUNDS

[76] Inventors: Russell H. Swenson, 623 Ohio Ave., St. Charles, Ill. 60174; Richard J. Windgassen, 610 Ironwood Cir., Venice, Fla. 34292

[21] Appl. No.: 09/192,021

[22] Filed: Nov. 13, 1998

[51] Int. Cl.[7] ............................. A61K 9/00; A61K 6/00; A61F 13/00; A61M 37/00
[52] U.S. Cl. ......................... 424/400; 424/401; 424/443; 604/23
[58] Field of Search ......................... 424/400, 45, 78.06, 424/401, 443, 447; 514/957; 602/41, 42, 43, 48; 604/23

[56] References Cited

U.S. PATENT DOCUMENTS

| | | | |
|---|---|---|---|
| 4,517,135 | 5/1985 | Szerenyi | 261/104 |
| 5,417,146 | 5/1995 | Zimmer | 99/323 |
| 5,473,161 | 12/1995 | Nix | 250/343 |
| 5,494,657 | 2/1996 | Swenson | 424/59 |
| 5,612,052 | 3/1997 | Shalaby | 424/426 |
| 5,624,645 | 4/1997 | Malley | 422/266 |
| 5,674,523 | 10/1997 | Cartmell | 424/445 |
| 5,725,491 | 3/1998 | Tipton | 604/43 |
| 5,851,544 | 12/1998 | Penska et al. | 424/401 |

OTHER PUBLICATIONS

Varghese et.al., Arch. Dermatol., 122 (1) 52–57 (1986).
Niinikoski et.al., Surg. Gynecol. Obstet., 133, 1003–1007 (1971).
A. Seidell, "Solubilities of Inorganic and Metallo–Organic Compounds", (1958).

*Primary Examiner*—Gollamudi S. Kishore
*Assistant Examiner*—Todd D Ware

[57] ABSTRACT

Compositions that express a pressure of carbon dioxide are beneficial when used for the care of wounds, and when externally applied to skin damaged by cuts, burns, abrasions, excessive radiation, or from rashes and similar dysfunctions.

11 Claims, No Drawings

COMPOSITIONS EXPRESSING A PRESSURE OF CARBON DIOXIDE FOR IMPROVED HEALING OF WOUNDS

BACKGROUND OF THE INVENTION

This invention relates to compositions expressing a pressure of carbon dioxide that assist in maintaining a beneficial pressure of carbon dioxide in the tissues of ulcer wounds. Such compositions also assist in maintaining a beneficial pressure of carbon dioxide in the skin and underlying tissue when applied to skin impaired by rashes or similar dysfunctions, or to skin traumatized by exposure to harsh conditions such as excessive heat or cold, ultraviolet radiation, or radiation therapy.

ULCER WOUNDS

As the population ages, the incidence of ulcer wounds is expected to rapidly increase. These wounds are costly to treat. Products that hasten the healing rate of ulcer wounds will reduce costs.

The cause of ulcer wounds, such as bed sores, stasis ulcers and diabetic ulcers, is usually impaired circulation. In affected areas, the skin and underlying tissue die. Though the ulcer wounds are mostly shallow, they can cover extensive areas on the body. Once formed, the ulcer wounds typically require months of medical care to heal.

The ulcer wounds heal gradually by growth of new tissue. Modern methods of treatment promote this tissue growth by keeping the wound clean, warm and moist. In early stages of treatment, the wound is freed of dead tissue and other debris (debridement) by procedures such as pressure flushing, wet to dry dressings, and surgery. Though essential, such debridement procedures damage the wound tissue by removing viable cells with the nonviable cells.

The ulcer wounds may require redressing several times a day. Between dressings, the wound is cleaned by flushing, most often with normal saline, a solution of 0.9% sodium chloride in water. Sometimes proprietary cleansing fluids are also employed. The dressing often consists of gauze moistened with normal saline and covered with a moisture proof covering. Other materials such as hydrogels, alginates and hydrocolloids also find application in wound dressings. None of these materials are currently manufactured to express a pressure of carbon dioxide that prevents or reduces loss of carbon dioxide from the healing tissues in the wound.

CARBON DIOXIDE AND WOUND HEALING

The carbon dioxide produced in the body from metabolism is eliminated through the process of respiration. However, carbon dioxide is an essential component of the body's pH buffer system. To maintain the optimal pH of 7.35 to 7.45 in the blood and tissues, the respiratory system regulates the pressure of carbon dioxide in the body at about 40 mm (40 mm of mercury) at 37 degrees centigrade. As the pressure of carbon dioxide decreases, the pH will increase, and a condition known as alkalosis will be reached. At a carbon dioxide pressure of 25 mm, for example, the pH will be about 7.52, a harmful degree of alkalosis.

The blood and tissues inside the body are readily permeable to carbon dioxide. The outside of the body is covered with skin. The skin is relatively impermeable to carbon dioxide. Thus the skin protects the underlying tissues from an excessive loss of carbon dioxide. Even lightly abraded skin becomes permeable to carbon dioxide. Because the carbon dioxide pressure in the atmosphere is very low, about 0.2 mm, there will be a net transfer of carbon dioxide from the abraded skin area into the air.

The process of cleansing ulcer wounds exposes the wound tissue to the air and facilitates the loss of carbon dioxide. During dressing changes, the wounds are also exposed to air. Flushing the wounds with carbon dioxide free fluids causes a rapid transfer of carbon dioxide from the wound tissue. Once a dressing is in place, flow of carbon dioxide from the tissues will begin to accumulate under the dressing, and the pressure of carbon dioxide will begin to increase. However, flow of carbon dioxide from the wound tissue cannot fully cease until the wound materials have absorbed sufficient carbon dioxide to approach the same carbon dioxide pressure as the wound tissue. Some wound coverings are permeable to carbon dioxide. Losses through the wound covering will further delay build up of desirable pressures of carbon dioxide in the dressing.

Studies have failed to demonstrate that wound coverings permeable to atmospheric oxygen facilitate wound healing by providing more oxygen to the wound tissues. Wound coverings more permeable to oxygen will often be even more permeable to carbon dioxide, Although this is just a theory, the benefit of additional oxygen under oxygen permeable dressings may not compensate for harm done by increased loss of carbon dioxide.

In the medical literature, the pressure of carbon dioxide expressed by blood and tissue is often stated as a "partial pressure". The blood and tissues express pressures of other gases, too, of which oxygen is most important. Similarly, the compositions of this invention can also express pressures of other gases. In most cases these other expressed gas pressures will have little significance. For example, suppose water at 25 degrees centigrade is equilibrated with a 760 mm atmosphere consisting of 40 mm pressure of carbon dioxide with the remaining 720 mm pressure consisting of water vapor, and the gases oxygen, nitrogen and argon in their normal atmospheric ratios. The water will then express pressures of 40 mm of carbon dioxide, about 145 mm of oxygen, about 541 mm of nitrogen, about 7 mm of argon and 27 mm of water vapor. The amounts of nitrogen and oxygen actually dissolved in the water will be small, about 5.5 ml of oxygen per liter and about 12 ml of nitrogen per liter. These amounts are believed too small to have any measurable effect on performance of compositions of the subject invention. The compositions of this invention will express a pressure of carbon dioxide, and may or may not express significant pressures of other chemical species. The term "partial pressure" is accordingly not used in this disclosure.

PRIOR ART

It is surprising that prior art failed to recognize the benefits of maintaining a pressure of carbon dioxide in the wound that is similar to that of body tissues.

For example, normal saline is usually preferred over plain water for cleansing and dressing of ulcer wounds. The reason is that the salt concentration of 0.9% in normal saline confers on that fluid an osmotic pressure similar to that of fluid in wound tissue. This similarity avoids the harmful transfer of water from the normal saline across cell membranes into the cell. Normal saline that expresses an appropriate pressure of carbon dioxide would in addition avoid transfer of carbon dioxide out of the cell.

A wide variety of therapeutic, diagnostic and pharmacological agents have been suggested for inclusion in wound dressings to promote healing. Tipton in U.S. Pat. No. 5,725, 491, lists biocides, vitamins, minerals, and analgesics, among others. Many of such additives have been found detrimental because, for example, they may prove irritating, promote growth of microorganisms or cause allergies. Carbon dioxide has not been suggested as an additive despite the potential benefits and absence of harmful side effects.

Medical research teams have studied how carbon dioxide pressures change in wounds, but have not suggested the advantages of using compositions expressing a pressure of carbon dioxide in wound care products. For example, Varghese et.al., Arch Dermatol 122 (1) 52–57 (1986), measured the pressures of carbon dioxide in wound fluid that had accumulated under two types of dressings on ulcer wounds. After 24 hours, the wound fluid pressure of carbon dioxide was 66.5 mm with one dressing type and greater than 100 mm for the other dressing type. Niinikoski et. al. Surg Gynecol Obstet 133, 1003–1007 (1971), demonstrated that the pressure of carbon dioxide in wound fluid in experimental wounds in rats increased over three days to over 100 mm, and did not decrease to normal pressure of 47 mm until 30 days elapsed. The results of both investigators show that the surface of wound tissue is highly permeable to carbon dioxide. Niinikoski suggested that the relatively high pressure of carbon dioxide early in the wound healing process could result from limited blood supply to the rapidly growing wound tissue. If the blood supply is too limited to remove surplus carbon dioxide from wound tissue, then the blood supply would likely also prove incapable of delivering sufficient carbon dioxide to maintain a normal carbon dioxide pressure in wound tissue exposed to air, wound dressing material or to cleansing fluids.

Varghese suggested that a low pH in wounds would retard growth of bacteria. He also suggested that carbon dioxide might provide a desirably low pH. Both Varghese and Niinikoski showed that wound fluid pH was not substantially reduced by carbon dioxide because the wound fluid is buffered. However, the carbon dioxide in compositions of this invention would reduce the pH of many wound dressing materials, retarding bacterial growth and perhaps reducing unpleasant odor.

Tipton has suggested carbon dioxide as an aerosol propellant or co-propellant to apply a biodegradable film dressing on tissue. Carbon dioxide is a common aerosol propellant and has likely been employed in commercial products applied to skin abrasions, burns or cuts to relieve pain or prevent infection. However, the beneficial effect of carbon dioxide in these formulations for reducing loss of carbon dioxide from wounds or other skin damaged areas was not anticipated. In addition, most of the carbon dioxide in atomized aerosol particles would be transferred to the air as the particles moved to the skin.

SUMMARY OF THE INVENTION

Accordingly, it is a primary object of the present invention to provide compositions that help maintain a beneficial partial pressure of carbon dioxide in ulcer wound tissue when said compositions are used for cleansing the ulcer wound or used as a component of the ulcer wound dressing. This object is accomplished by formulating compositions that express a pressure of carbon dioxide at the wound surface, or under the dressing, that significantly assists in reducing undesirable flow of carbon dioxide from the wound tissue.

Another object of the present invention is to provide solutions, creams, lotions, ointments and other topical dressings for damaged skin that help maintain optimal pressures of carbon dioxide in the skin and underlying tissue.

DETAILED DESCRIPTION OF THE INVENTION

The invention is compositions that provide pressures of carbon dioxide in a wound or to damaged skin that promote healing. In principle any fluid, polymeric or solid material, or combinations of these could be modified to express a carbon dioxide pressure by, for example, exposure to an atmosphere having the desired pressure of carbon dioxide until equilibrium was attained.

For practical use, the composition must not only express a pressure of carbon dioxide, but must be capable of supplying amounts of carbon dioxide that will generate a useful pressure of carbon dioxide under a wound dressing or near damaged skin. Solids such as glass or sodium chloride adsorb only superficial amounts of carbon dioxide on their surfaces; even if they were equilibrated with high pressures of carbon dioxide, they would not be useful.

Most liquids suitable for wound care or skin care applications would find use in the subject invention. Examples include water and organic compounds, and combinations of these. The organic liquids include alcohols, aldehydes, amides, certain amines, esters, ethers, hydrocarbons, olefins and polyols. Solid compounds that dissolve become part of the liquid phase and contribute to solubilization of carbon dioxide. Liquids with modified properties such as emulsions, gels, hydrogels, lotions, ointments and suspensions are also useful.

That useful amounts of carbon dioxide dissolve in most liquids, or liquid containing formulations, can be assessed from published solubility data. Seidell (A. Seidell, "Solubilities of Inorganic and Metal-organic Compounds" Fourth Edition (1958) provides a large compilation of carbon dioxide solubilities. Values of carbon dioxide solubilities noted in this paragraph are given as ml. of carbon dioxide that one liter of liquid dissolves under 760 mm (1 atmosphere) of carbon dioxide pressure. Measurements of carbon dioxide solubility in Seidell are not all reported at the same temperature. However, the solubility of carbon dioxide in liquids is about 50% higher at 20 degrees centigrade than at 40 degrees centigrade. Thus, the data are sufficient to support the argument that all fluids used or potentially used in wound and skin care products would dissolve useful amounts of carbon dioxide. Carbon dioxide solubility in water at 25 degrees centigrade is 759 ml; in water containing 0.9% sodium chloride, solubility declines to 728 ml. Thus the important wound treatment fluid, normal saline, dissolves only slightly less carbon dioxide than water. It is reported in Seidell that the solubility of carbon dioxide in blood is 93–94% of its water solubility. At 20 degrees centigrade, ethyl alcohol dissolves 2840 ml of carbon dioxide, water at 20 degrees centigrade dissolves 878 ml, water containing 6% ethyl alcohol dissolves 900 ml, and water containing 12% alcohol dissolves 1104 ml. A 285 SUS viscosity white mineral oil (USP Grade 28) dissolves 841 ml of carbon dioxide at 0 degrees centigrade. On the other hand, cottonseed and other fatty oils dissolve only about 100 ml of carbon dioxide at 40 degrees centigrade. The data in Seidell suggests that hydrocarbon or largely hydrocarbon oils will contain about 0.6 to about 1.2 mole % carbon dioxide at 20 degrees centigrade. Thus carbon dioxide solubility in hydrocarbons decreases proportionately to increasing average molecular weight. Accordingly, heptane, with a molecular weight of 100, dissolves 1915 ml of carbon dioxide at 20 degrees centigrade; the 28USP Grade white mineral oil with a molecular weight of about 350 dissolves an estimated 560 ml at 20 degrees centigrade; and cottonseed oil and other fatty oils with molecular weights around 800 dissolve an estimated 150 ml of carbon dioxide at 20 degrees centigrade.

Boyle's law states that the solubility of a gas in a liquid is proportional to the pressure of that gas. One preferred embodiment of this invention is a normal saline solution that expresses a carbon dioxide pressure of about 50 mm at a temperature of 37 degrees centigrade, the normal human body temperature. A liter of normal saline dissolves 550 ml of carbon dioxide at 37 degrees centigrade under 760 mm carbon dioxide pressure. Thus, a normal saline solution exhibiting a carbon dioxide pressure of 50 mm requires 50/760×550 ml=36 ml of carbon dioxide per liter. This volume of carbon dioxide weighs only 0.071 grams, and in the dissolved state occupies an almost negligible volume. Many formulations will thus require no reformulation when carbon dioxide is added to them to meet the claims of this invention.

Besides liquids, some elastomers and solids may have applications in compositions of this invention. Certain elastomers such as natural rubber can reversibly absorb carbon dioxide, and could supply carbon dioxide to a wound when used as a wound covering. Charcoal also reversibly absorbs significant amounts of carbon dioxide. Charcoal that contained carbon dioxide when employed as a component of a wound dressing would not only supply carbon dioxide, but would also absorb foul odors.

Composite materials, such as preassembled wound dressings, could also be used in this invention, if one or more of its component materials, such as elastomer or hydrogel, absorbed significant amounts of carbon dioxide. One manner of converting the composite to a composition of this invention would be to place the composite in a carbon dioxide impervious container with a predetermined amount of carbon dioxide, and storing the container for an appropriate time before use.

Many existing formulations could be converted to compositions of this invention by including carbon dioxide in the formulation, or sometimes by exposing the completed formulation to carbon dioxide gas. The addition of carbon dioxide to some formulations will have adverse effects, primarily because carbon dioxide behaves as a very weak acid. Those skilled in the art will be able to recognize the possible problems, and in many cases adjust the formulations to overcome the problems.

The carbon dioxide in the compositions of this invention can be generated chemically. EXAMPLE 2 illustrates such a procedure for normal saline, wherein the reacting chemicals yield both the required carbon dioxide as well as a portion of the required sodium chloride. Malley in U.S. Pat. No. 5,624,645 discloses an apparatus wherein carbon dioxide gas is generated from chemicals in a chamber separate from liquid that absorbs the carbon dioxide.

However, economical gaseous, liquid and solid sources of purified carbon dioxide are readily available. Inexpensive beverage quality grade carbon dioxide is sufficiently pure for manufacture of the materials of this invention.

Normally the compositions of this invention will be used on body surfaces that have a temperature near the human body temperature of 37 degrees centigrade. For this reason we have specified pressures of carbon dioxide for compositions of this invention at 37 degrees centigrade. Those skilled in the art will recognize that a composition expressing a pressure of carbon dioxide at 37 degrees centigrade will express a higher pressure at higher temperatures and a lower pressure at lower temperatures.

The carbon dioxide pressure selected for compositions of this invention will depend on their application. For example, in normal saline used for flushing or cleansing of wounds, an expressed carbon dioxide pressure of 40–50 mm at 37 degrees centigrade would normally be satisfactory.

If the normal saline was used as a component of a wound dressing, a higher expressed pressure of carbon dioxide may be desirable. During the dressing operation, some carbon dioxide may escape into the air. The finished dressing will contain other materials such as gauze, tape or hydrated hydrogel that will absorb significant amounts of carbon dioxide. The air space under the bandage must also be supplied with carbon dioxide. According to Boyle's Law, as the normal saline solution supplies carbon dioxide during the dressing operation to the air, and to other components of the dressing, its own exhibited pressure of carbon dioxide decreases. Thus the initial expressed pressure of carbon dioxide would preferably be sufficient to yield a pressure of about 40 mm in the finished wound. Of course, normal saline expressing a pressure of 40 mm at 37 degrees centigrade would still prove superior to ordinary normal saline, because it would still contribute some useful pressure of carbon dioxide in the wound.

Determination of the carbon dioxide pressure in compositions of this invention can be accomplished with readily available procedures. Tonometers for monitoring the carbon dioxide pressure of blood are in general use. Szerenyi in U.S. Pat. No. 4,517,135 discloses procedures for in line monitoring of carbon dioxide in fluids made in continuous manufacture. The effective carbon dioxide pressure in a preassembled wound dressing, thick hydrogel or other material in which direct measurement is difficult, can be determined by allowing the material to equilibrate with a small gas space. The pressure of carbon dioxide measured in the gas space will be substantially the same pressure initially present in the material.

The subject invention can be practiced if only the pressure of carbon dioxide expressed by the composition is known at 37 degrees centigrade. The manner in which the expressed pressure of carbon dioxide of the composition varies with temperature need not be known. The actual amount of carbon dioxide in a composition required to achieve a given pressure of carbon dioxide also need not be known. Such information may, however, assist in formulating and quality control, and can be readily determined by those skilled in the art.

Some precautions must be taken to avoid loss of carbon dioxide of compositions of this invention during storage. Compositions packaged in sealed metal or glass containers would retain the initial carbon dioxide pressure for long storage periods. Plastic packaging materials are available that have sufficiently low permeability to carbon dioxide for acceptable storage life. Nix in U.S. Pat. No. 5,473,161, for example, discloses that PET bottles of the type currently used for carbonated beverages, undergo a loss of about 10% of contained carbon dioxide per month. Nix also discloses a procedure for monitoring the carbon dioxide loss without opening the PET container. Capped metal or plastic tubes would be particularly advantageous for gels, ointments and similar compositions that may be used in small portions at a time.

While several embodiments and variations of the present invention for compositions expressing a partial pressure of carbon dioxide for improved healing of wounds are described in detail herein, it should be apparent that the disclosure and teachings of the present invention will suggest many alternative compositions to those skilled in the art.

EXAMPLE 1

This example illustrates the continuous preparation of a water solution that expresses a pressure of carbon dioxide of 40 mm at 37 degrees centigrade from gaseous carbon dioxide and water.

To a 50 gallon agitated mixing vessel is charged about 40 gallons of distilled water at a temperature below about 27 degrees centigrade. An atmosphere of carbon dioxide gas is maintained at the agitated water surface. A side stream of liquid from the vessel is continually passed through an infra red analyzer to continuously monitor the concentration of carbon dioxide. When the concentration of carbon dioxide in the water in the vessel reaches 0.0590 grams per liter of solution, more distilled water is added, and the rates of addition of distilled water and draw off of product are adjusted to maintain the original level of liquid in the tank at a concentration of 0.0590 grams of carbon dioxide per liter.

EXAMPLE 2

This example illustrates the preparation of a normal saline solution that expresses a pressure of carbon dioxide of 40 mm at 37 degrees centigrade, using chemicals to generate the carbon dioxide as well as a portion of the sodium chloride.

To a one liter volumetric flask is added 8.92 grams of sodium chloride and 0.1126 grams of sodium bicarbonate. About 500 ml of distilled water is added, and the fluid is swirled to dissolve the solids. There is then added 13.41 ml of 0.1 normal hydrochloric acid. Distilled water is added to the one liter mark, and the flask is capped and inverted twenty times to mix the contents.

EXAMPLE 3

This example illustrates the conversion of a hydrogel preparation intended for use in wounds into a composition that expresses a pressure of carbon dioxide of 100 mm at 37 degrees centigrade. The advantage of this procedure is that no information about the solubility of carbon dioxide in the hydrogel is required, nor is a special instrument required to measure the pressure of carbon dioxide in the finished composition.

To a five liter autoclave is added 2500 grams of a hydrated hydrogel. The air in the autoclave is pumped out and replaced by carbon dioxide at 100 mm pressure. The autoclave contents are heated and maintained at 37 degrees centigrade. The autoclave is stirred and carbon dioxide is admitted to the autoclave to maintain a pressure of 100 mm. When No additional carbon dioxide is taken up, agitation is stopped and the product is pumped from the autoclave, while maintaining 100 mm of carbon dioxide pressure in the autoclave. The product is packaged in containers substantially impervious to carbon dioxide and water.

EXAMPLE 4

This example illustrates how a preassembled wound dressing may be converted to a composition of the subject invention.

Preassembled wound dressings, consisting of an outer moisture resistant wound covering material that is bonded to a layer of gauze impregnated with a hydrated hydrogel, are placed in plastic bags substantially impervious to carbon dioxide and water. The plastic bags are partially sealed and stacked in an autoclave with the open ends in the up position. Carbon dioxide gas at atmospheric pressure is admitted into the bottom of the autoclave and displaced air is allowed to exit from a line at the top of the autoclave. When all air is expelled, the autoclave is sealed, and the pressure of carbon dioxide is maintained at 760 mm until no more carbon dioxide is absorbed. The top of the autoclave is removed, and a flow of carbon dioxide through the bottom of the autoclave is maintained to keep air from entering the bags in the autoclave. The bags are sealed before removal from the autoclave. Preassembled wound dressings treated in this manner express a pressure of one atmosphere (760 mm) of carbon dioxide.

EXAMPLE 5

This example shows how a largely water free, non-polar formulation can be converted into composition that expresses a carbon dioxide pressure in the range of 300 to 400 mm at 37 degrees centigrade.

Five kilograms of the skin care formulation described in EXAMPLE 1 in Swenson, U.S. Pat. No. 5,494,657 is charged into a ten liter autoclave. The air in the autoclave is pumped out and replaced with carbon dioxide at 760 mm pressure. The autoclave is heated to 55 degrees centigrade. The autoclave is agitated and the pressure in the autoclave is maintained at 760 mm pressure with carbon dioxide until no more carbon dioxide is absorbed. Agitation is stopped. A pressure of 760 mm of carbon dioxide is maintained in the autoclave while the product is withdrawn and packaged in containers substantially impermeable to carbon dioxide.

We claim:

1. A method for treating, or reducing the extent of, alkalosis in tissues at the surface of wounds, or underlying the surface of wounds, which results when said wound surface is exposed to air, or to aqueous solutions which express a pressure of carbon dioxide less than about 30 mm of mercury, which method comprises administering to the wound an aqueous wound care composition that expresses a pressure of carbon dioxide from about 10 mm of mercury to about 135 mm mercury.

2. The method of claim 1 wherein the composition of the aqueous wound care composition comprises water and carbon dioxide.

3. The method of claim 1 wherein the composition of the aqueous wound care composition comprises a water solution of carbon dioxide that expresses a carbon dioxide pressure of about 30 mm to about 55 mm of mercury when said composition is at a temperature of 37 degrees centigrade.

4. The method of claim 1 wherein the composition of the aqueous wound care composition comprises a water solution of about 0.5 to about 1.2 wt. percent of sodium chloride, and carbon dioxide.

5. The method of claim 1 wherein the composition of the aqueous wound care composition comprises a water solution of about 0.5 to about 1.2 wt. percent of sodium chloride, and carbon dioxide, that expresses a carbon dioxide pressure Of about 30 mm to about 55 mm of mercury, when said composition is at a temperature of 37 degrees centigrade.

6. The method of claim 1 wherein the composition of the aqueous wound care composition comprises a water solution of about 0.5 to about 1.2 wt. percent of sodium chloride, buffered to a pH range of about 5 to about 8 with buffers selected from the group sodium, potassium or ammonium salts of boric, phosphoric, citric or carbonic acids.

7. The method of claim 1 wherein the composition of the aqueous wound care composition comprises a water solution of about 0.5 to about 1.2 wt. percent of sodium chloride, buffered to a pH range of about 5 to 8 with buffers selected from the group, sodium, potassium, or ammonium salts of boric, phosphoric, citric or carbonic acids, that expresses a carbon dioxide pressure of about 30 mm to about 55 mm of mercury, when said composition is at a temperature of 37 degrees centigrade.

8. The method of claim 1 wherein the composition of the aqueous wound care composition is a hydrated hydrogel, and carbon dioxide.

9. The method of claim 1 wherein the composition of the aqueous wound care composition is a hydrated hydrogel, and carbon dioxide, and that expresses a carbon dioxide pressure of about 30 mm to about 55 mm of mercury, when said composition is at a temperature of 37 degrees centigrade.

10. A method for treating, or reducing the extent of, alkalosis in tissues at the surface of wounds, or tissues underlying the surface of wounds, which results when said wound surface is exposed to air, or to aqueous solutions which express a pressure of carbon dioxide less than about 30 mm of mercury, which method comprises administering to the wound a wound care composition that is an emulsion of oil and water that expresses a pressure of carbon dioxide from about 10 mm of mercury to about 135 mm mercury.

11. A method for treating, or reducing the extent of, alkalosis in tissues at the surface of wounds, or tissues underlying the surface of wounds, which results when said wound surface is exposed to air, or to aqueous solutions which express a pressure of carbon dioxide less than about 30 mm of mercury, which method comprises administering to the wound a non aqueous wound care composition that expresses a pressure of carbon dioxide from about 10 mm of mercury to about 135 mm mercury.

* * * * *